(12) United States Patent
Ohba et al.

(10) Patent No.: US 9,513,218 B2
(45) Date of Patent: Dec. 6, 2016

(54) OPTICAL SENSOR AND IMAGE FORMING DEVICE INCORPORATING THE SAME

(71) Applicants: Yoshihiro Ohba, Sendai (JP); Satoru Sugawara, Sendai (JP); Toshihiro Ishii, Sendai (JP); Fumikazu Hoshi, Sendai (JP)

(72) Inventors: Yoshihiro Ohba, Sendai (JP); Satoru Sugawara, Sendai (JP); Toshihiro Ishii, Sendai (JP); Fumikazu Hoshi, Sendai (JP)

(73) Assignee: RICOH COMPANY, LTD., Tokyo (JP)

( * ) Notice: Subject to any disclaimer, the term of this patent is extended or adjusted under 35 U.S.C. 154(b) by 210 days.

(21) Appl. No.: 14/199,056

(22) Filed: Mar. 6, 2014

(65) Prior Publication Data

US 2014/0268151 A1 Sep. 18, 2014

(30) Foreign Application Priority Data

Mar. 13, 2013 (JP) .................................. 2013-049810

(51) Int. Cl.
*G01N 21/47* (2006.01)
*G03G 15/00* (2006.01)
*H01J 3/14* (2006.01)
*G01J 1/42* (2006.01)
(Continued)

(52) U.S. Cl.
CPC .............. *G01N 21/55* (2013.01); *G01N 21/21* (2013.01); *G03G 15/50* (2013.01); *G03G 15/5029* (2013.01); *G01N 21/474* (2013.01); *G01N 2021/556* (2013.01);
(Continued)

(58) Field of Classification Search
CPC ........ G01N 21/17; G01N 21/21; G01N 21/86; G01N 21/55; G01N 21/474; G01N 2021/4792; G01N 2021/217; G01N 2021/556; G03G 15/6594; G03G 15/6591; G03G 15/50; G03G 15/5029; G03G 2215/00751; G03G 2215/00616; G03G 2215/0132; G03G 2215/00738
(Continued)

(56) References Cited

U.S. PATENT DOCUMENTS 6,356,347 B1 3/2002 Watanabe et al.
9,267,886 B2 * 2/2016 Ohba ................. G03G 15/5029
2001/0010363 A1 8/2001 Watanabe et al.
(Continued)

FOREIGN PATENT DOCUMENTS

JP 7-172635 7/1995
JP 2005-156380 6/2005
(Continued)

*Primary Examiner* — Tarifur Chowdhury
*Assistant Examiner* — Sunghee Y Gray
(74) *Attorney, Agent, or Firm* — Cooper & Dunham LLP

(57) ABSTRACT

An optical sensor includes a light source to illuminate a linear polarization in a first direction, a first optical detector disposed on a path of a light illuminated from the light source and specularly reflected by an object, a first optical element to separate the light reflected by the object into a linear polarization in the first direction and a linear polarization in a second direction orthogonal to the first direction, a second optical detector to receive the linear polarization in the second direction separated by the first optical element, and a processor to obtain an amount of the light specularly reflected by the object on the basis of an output signal of the first optical detector and an output signal of the second optical detector.

11 Claims, 23 Drawing Sheets

(51) Int. Cl.
*G01N 21/55* (2014.01)
*G01N 21/21* (2006.01)

(52) U.S. Cl.
CPC ............ *G03G 2215/00616* (2013.01); *G03G 2215/00738* (2013.01); *G03G 2215/0132* (2013.01)

(58) Field of Classification Search
USPC ....... 356/369; 347/224; 359/204.1; 362/227, 362/235; 370/254, 312; 399/45; 250/216, 208.2
See application file for complete search history.

(56) References Cited

U.S. PATENT DOCUMENTS

| | | | |
|---|---|---|---|
| 2001/0013935 A1 | 8/2001 | Watanabe et al. | |
| 2006/0018539 A1* | 1/2006 | Sato | G06K 9/36 382/173 |
| 2011/0228035 A1 | 9/2011 | Ishii et al. | |
| 2011/0261139 A1 | 10/2011 | Hoshi et al. | |
| 2011/0267415 A1 | 11/2011 | Ohba et al. | |
| 2012/0134693 A1* | 5/2012 | Hoshi | G03G 15/5029 399/45 |
| 2013/0057861 A1 | 3/2013 | Ishii et al. | |
| 2013/0194573 A1* | 8/2013 | Ohba | G03G 15/5029 356/369 |
| 2013/0216245 A1 | 8/2013 | Hoshi et al. | |
| 2013/0216246 A1 | 8/2013 | Hoshi et al. | |
| 2013/0216247 A1 | 8/2013 | Oba et al. | |
| 2013/0228674 A1 | 9/2013 | Oba et al. | |
| 2013/0235377 A1 | 9/2013 | Ishii et al. | |

FOREIGN PATENT DOCUMENTS

| | | | |
|---|---|---|---|
| JP | 3830267 | | 7/2006 |
| JP | WO 2012070693 | * 5/2012 | ......... G01B 11/0625 |
| JP | 2012-127937 | | 7/2012 |

* cited by examiner

OPTICAL SENSOR AND IMAGE FORMING DEVICE INCORPORATING THE SAME

CROSS REFERENCE TO RELATED APPLICATION

The present application is based on and claims priority from Japanese Patent Application No. 2013-049810, filed on Mar. 13, 2013, the disclosure of which is hereby incorporated by reference in its entirety.

BACKGROUND OF THE INVENTION

1. Field of the Invention

The present invention relates to an optical sensor suitable for identifying a target in question and an image forming device incorporating such an optical sensor.

2. Description of the Related Art

An image forming device such as a digital copier or laser printer transfers a toner image onto the surface of a recording medium including a print paper, applies heat and pressure under a certain condition to fuse it, and forms an image. A heat amount and a pressure amount at the fusing need to be taken into account for forming an image. Particularly, to form high-quality images, a fusing condition needs to be set individually for kinds of recording medium.

This is because the quality of image is greatly affected by the material, thickness, moisture, smoothness, and coating of a recording medium. For example, in terms of smoothness, a toner fixation rate on the depressed portion of a print paper decreases depending on a fusing condition. Color unevenness in an image may occur unless an image is fused under a proper condition according to a recording medium.

Further, along with a progress of image forming devices and diversified representations, the types of recording media are various and there are more than several hundred different kinds of print papers. Moreover, in each kind of paper a variety of brands with different thicknesses and basis weights are available. It is necessary to set a detailed fusing condition for each brand of paper in order to generate high-quality images.

There has been an increase in the number of brands of plain paper, coated paper such as gross coated paper, matt coated paper, and art coated paper, plastic sheet, and special paper having an embossed surface.

Currently, users have to set a fusing condition of an image forming device in printing. Users are required to have knowledge to recognize different types of paper and it is troublesome for them to input settings for a kind of a paper in use. Optimal images cannot be acquired if there is an error in the settings.

An optical method in which a light is irradiated to a recording medium to detect a brand of the recording medium or a state of the surface thereof from a reflective or transmissive light beam by the recording medium is known.

For example, Japanese Patent Application Publication No. 2005-156380 (Reference 1) discloses a determining device to determine a kind of a recording medium using reflective and transmissive lights.

Japanese Patent No. 3362360 (Reference 2) discloses a printer having a determiner to separate an S-polarization component and a P-polarization component from a reflected light by a document to electrically determine a kind, presence or absence, or state of the surface of the document.

Japanese Patent Application Publication No. 2012-127937 (Reference 3) discloses an optical sensor to specify a brand of a paper from a light amount of P-polarization components of an internal diffuse reflection of light and that of S-polarization components of a surface specular reflection of light.

Japanese Patent No. 3830267 (Reference 4) discloses a surface inspection device which detects a roughness of a specimen surface from a reflected intensity of S-polarization components and that of P-polarization components.

However, it is hard to accurately specify an object in question.

SUMMARY OF THE INVENTION

The present invention aims to provide an optical sensor which can accurately specify an object in question.

According to one embodiment, an optical sensor comprises a light source to illuminate a linear polarization in a first direction, a first optical detector disposed on a path of a light illuminated from the light source and specularly reflected by an object, a first optical element to separate the light reflected by the object into a linear polarization in the first direction and a linear polarization in a second direction orthogonal to the first direction, a second optical detector to receive the linear polarization in the second direction separated by the first optical element, and a processor to obtain an amount of the light specularly reflected by the object on the basis of an output signal of the first optical detector and an output signal of the second optical detector.

BRIEF DESCRIPTION OF THE DRAWINGS

Features, embodiments, and advantages of the present invention will become apparent from the following detailed description with reference to the accompanying drawings:

FIG. 7 shows reflections of light received by light receivers 14 and 15 when a light source 10 is turned on;

FIG. 8 shows reflections of light received by light receivers 14 and 15 when a light source 11 is turned on;

FIG. 9A shows reflections of light received by the light receiver 13 when the light source 10 is turned on while FIG. 9B shows the same when the light source 11 is turned on;

FIGS. 11A, 11B show reflections of light received by the respective light receivers when the light sources 10, 11 are concurrently turned on;

FIG. 12 shows reflections of light received by the light receivers 14 and 15 when a polarization beam splitter with a different property is used and the light source 10 is turned on;

FIG. 13 shows reflections of light received by the light receivers 14 and 15 when a polarization beam splitter with a different property is used and the light source 11 is turned on;

FIG. 15 shows reflections of light received by the light receivers of the optical sensor in FIG. 14 when the light source 10 is turned on;

FIG. 16 shows reflections of light received by the light receivers of the optical sensor in FIG. 14 when the light source 11 is turned on;

DETAILED DESCRIPTION OF THE PREFERRED EMBODIMENTS

Figure 1:
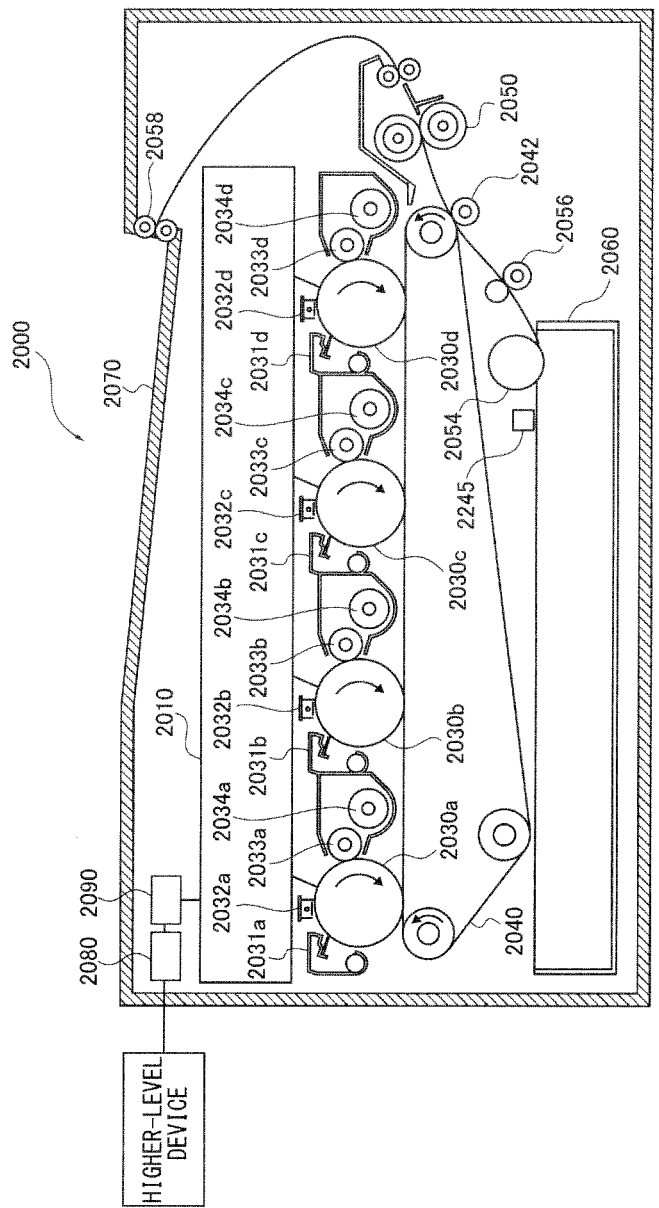
FIG. 1 schematically shows the structure of a color printer according to one embodiment.

Hereinafter, embodiments of the present invention will be described in detail with reference to the accompanying drawings. One embodiment of the present invention is described referring to FIG. 1 to FIG. 11B. Wherever possible, the same reference numbers will be used throughout the drawings to refer to the same or like parts. FIG. 1 schematically shows the structure of a color printer 2000 as an example of an image forming device according to one embodiment.

The color printer 2000 is a tandem multi-color printer to superimpose four color (black, cyan, magenta, yellow) images and generate a full-color image. It comprises an optical scanner 2010, four photoreceptor drums 2030a, 2030b, 2030c, 2030d, four cleaning units 2031a, 2031b, 2031c, 2031d, four charging units 2032a, 2032b, 2032c, 2032d, four developing rollers 2033a, 2033b, 2033c, 2033d, a transfer belt 2040, a transfer roller 2042, a fuser 2050, a feed roller 2054, a discharge roller 2058, a paper tray 2060, a discharge tray 2070, a communication controller 2080, an optical sensor 2245, and a printer controller 2090 to collectively control the above elements.

The communication controller 2080 controls bi-directional communication with a higher-level device such as personal computer via network.

The printer controller 2090 comprises a CPU, an ROM containing a program written in a code decodable by the CPU and various kinds of data necessary for the execution of the program, an RAM as work memory, an amplification circuit, and an A/D converter circuit. It controls the respective elements in accordance with a request from the higher-level device and transmits image information from the higher-level device to the optical scanner 2010.

The photoreceptor drum 2030a, charging unit 2032a, developing roller 2033a, and cleaning unit 2031a form an image station (hereinafter, K station) in which black images are generated.

The photoreceptor drum 2030b, charging unit 2032b, developing roller 2033b, and cleaning unit 2031b form an image station (hereinafter, C station) in which cyan images are generated.

The photoreceptor drum 2030c, charging unit 2032c, developing roller 2033c, and cleaning unit 2031c form an image station (hereinafter, M station) in which magenta images are generated.

The photoreceptor drum 2030d, charging unit 2032d, developing roller 2033d, and cleaning unit 2031d form an image station (hereinafter, Y station) in which yellow images are formed.

Each photoreceptor drum includes a photoreceptive layer on the surface which is scanned, and is rotated by a not-shown rotational mechanism in the direction indicated by the arrows in FIG. 1.

Each charging unit evenly charges the surface of a corresponding photoreceptor drum.

The optical scanner 2010 scans the charged surfaces of the photoreceptor drums with lights modulated for the four colors on the basis of multi-color (black, cyan, magenta, yellow) image information from the printer controller 2090. Thereby, latent images corresponding to the image information are formed on the surfaces of the photoreceptor drums and moved towards the corresponding developing rollers along with the rotation of the photoreceptor drums.

Toner from not-shown toner cartridges is thinly, evenly coated on the surfaces of the developing rollers along with the rotation thereof. When the photoreceptor drums contact the developing rollers, the toner is attached only to portions of the photoreceptor drums illuminated with the lights. Thus, the latent images on the photoreceptor drums are visualized to toner images by the developing rollers. The toner images are transferred to the transfer belt 2040 together with the rotation of the photoreceptor drums.

Yellow, magenta, cyan and black toner images are transferred onto the transfer belt 2040 at a certain timing and superimposed to form a multi-color image.

The paper tray 2060 contains sheets of paper and the feed roller placed near the paper tray 2060 extracts them one by one and feeds them to a space between the transfer belt 2040 and transfer roller 2042. Thereby, the toner images are transferred from the transfer belt 2040 onto the sheets of paper and fed to the fuser 2050.

The fuser 2050 applies heat and pressure to the papers and fuses the toner thereon. Then, the fused papers are sent to the discharge tray 2070 via the discharge roller 2058 and accumulated thereon.

The cleaning units remove remnant toner from the corresponding photoreceptor drums. After the remnant toner is removed, the photoreceptor drums are returned to the positions facing the charging units.

The optical sensor 2245 is used for specifying a brand of the papers contained in the paper tray 2060.

Figure 2:
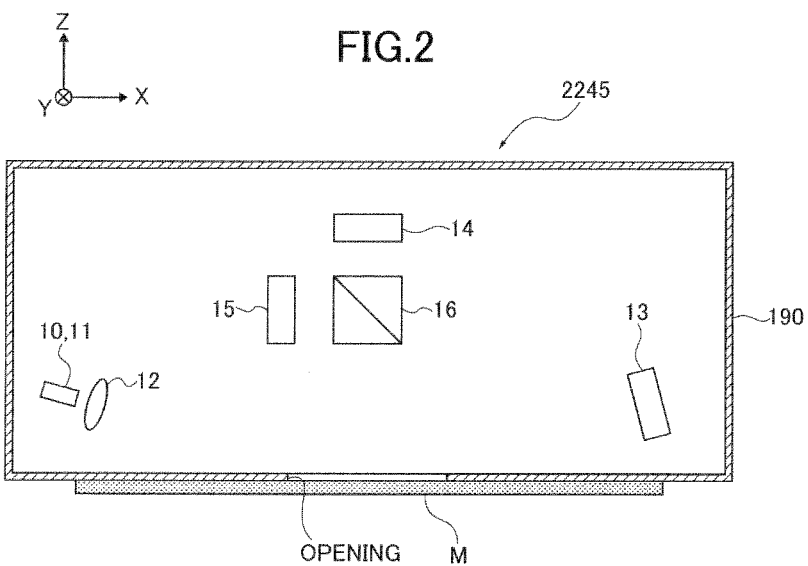
FIG. 2 shows the structure of an optical sensor in FIG. 1.
Figure 3:
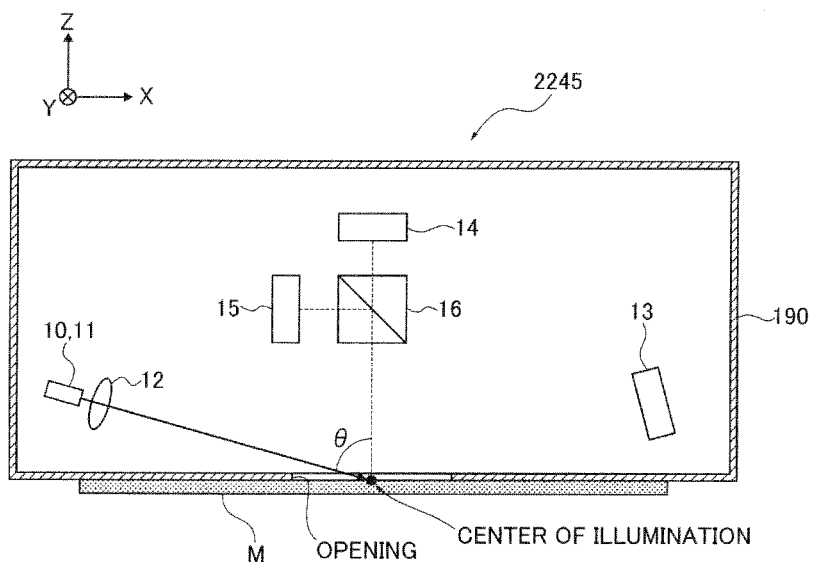
FIG. 3 shows an incidence angle of a light incident on a paper.

The optical sensor 2245 in FIG. 2 comprises two light sources 10, 11, a collimate lens 12, three light receivers 13, 14, 15, a polarization beam splitter 16, and a dark box 190 by way of example.

The dark box 190 is a metal box, for example, aluminum box and the surface thereof is subjected to black alumite treatment in order to reduce an influence from ambient light and stray light.

Herein, a direction orthogonal to the surface of a paper M is defined to be Z direction and the plane parallel thereto is defined to be an XY plane in an XYZ three-dimensional Cartesian coordinate system. The optical sensor 2245 is disposed on +Z side of the paper M.

The light sources 10, 11 are close to each other in Y axis direction and coincide with each other when orthographically illuminated on the XZ plane. The light source 10 is set to illuminate a linear polarization of S polarization components to the paper M while the light source 11 is set to illuminate a linear polarization of P polarization components thereto. The incidence angle θ (FIG. 3) of the light beams from the light sources on the paper M is 80 degrees. The light sources 10 and 11 are assumed to be at the same position for the sake of simplicity since they are very close to each other.

The light sources 10, 11 are individually controlled by the printer controller 2090 to alternatively turn on temporally. That is, they do not turn on concurrently.

The collimate lens 12 is placed on a path of light beams from the light sources 10, 11 to convert the light beams to approximately parallel light beams. Thereby, the light beams from the light sources can illuminate the paper M at an accurate incidence angle.

The light beams through the collimate lens 12 pass through an opening of the dark box 190 and illuminate the paper M. Herein, the center of an illuminated area of the paper M is referred to as the center of illumination and the light beams through the collimate lens 12 is referred to as illumination.

A plane including an incident light and a normal line of an interface of a medium at an incidence point is called an incident plane. If an incident light comprises several light beams, an incident plane exists for each light beam. Herein, the incident plane of the paper M is assumed to be an incident plane of a light beam incident on the center of illumination or an incident plane including the center of illumination and parallel to the XZ plane.

The polarization beam splitter 16 is placed on +Z side of the center of illumination to transmit a P polarization therethrough and reflect a S polarization.

Figure 4:
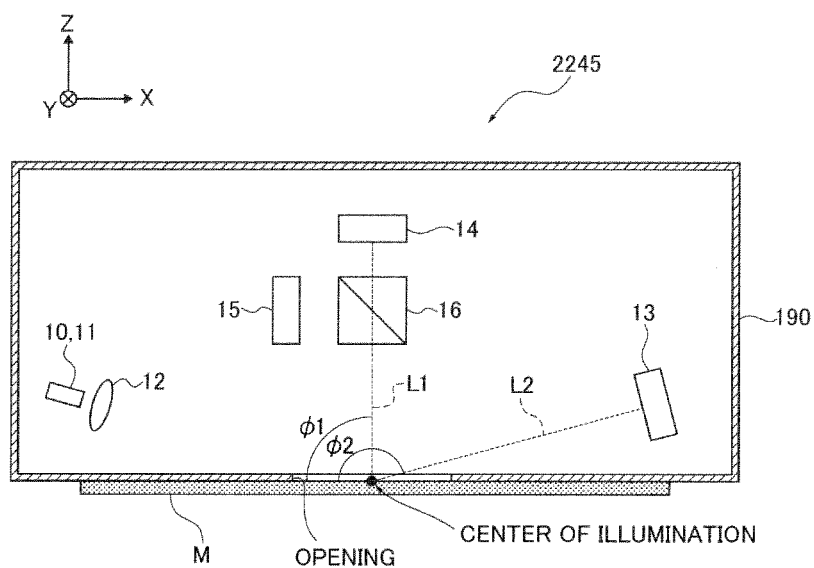
FIG. 4 shows the positions of three light receivers.

The light receiver 14 is placed on +Z side of the polarization beam splitter 16 and receives the light having transmitted through the polarization beam splitter 16. As shown in FIG. 4, a line L1 connecting the center of illumination and the centers of the polarization beam splitter 16 and light receiver 14 and the surface of the paper M make an angle ψ1 of 90 degrees.

The light receiver 15 is placed on −X side of the polarization beam splitter 16 and receives the light reflected by the polarization beam splitter 16.

The light receiver 13 is placed on +X side of the center of illumination in X direction. As shown in FIG. 4, a line L2 connecting the center of illumination and the center of the light receiver 13 and the surface of the paper M make an angle ψ2 of 170 degrees.

The centers of each light source and each light receiver and the center of illumination are on the same plane as the incident plane of the paper M, which will be hereinafter referred to as detection plane.

Figure 5:
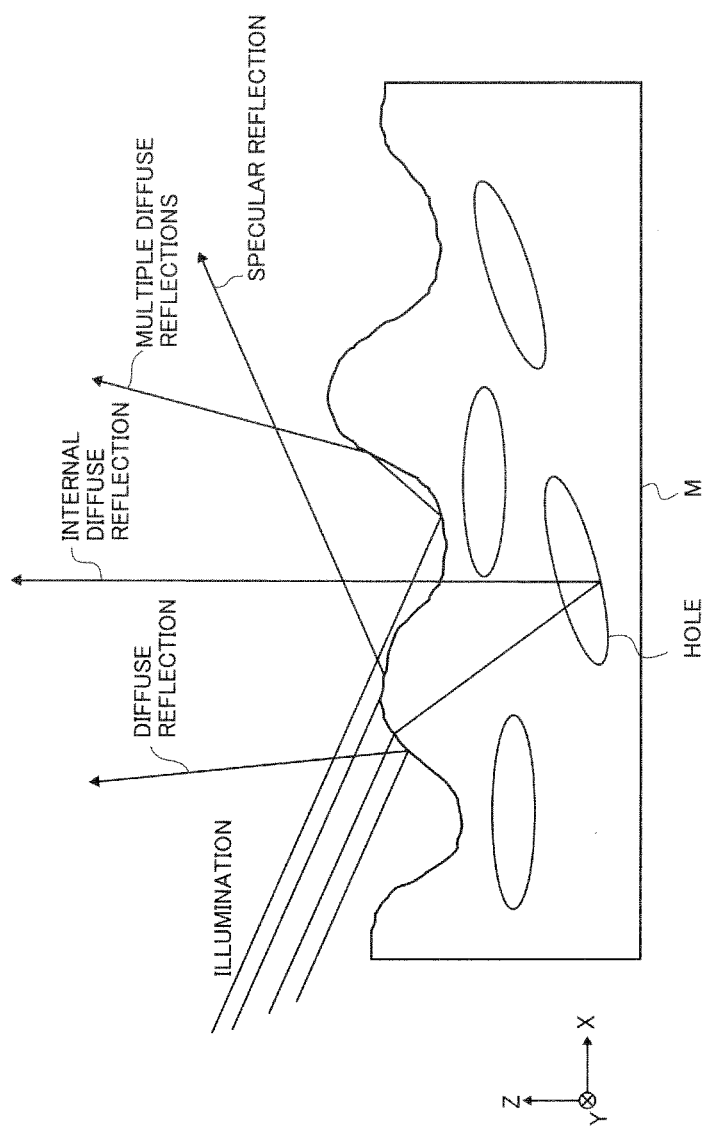
FIG. 5 shows various reflections of light.

The reflected light from the paper M is a reflection A by the surface of the paper M and a reflection B inside the paper M or an internal diffuse reflection. Further, the reflection A is (a) a specular reflection by the paper M, (b) a light diffused by one reflection or a diffuse reflection, and (c) a light diffused by multiple reflections by the uneven paper surface or a multiple diffuse reflections, as shown in FIG. 5.

With use of a general print paper as the paper M, light is reflected repeatedly at a large number of times by the interface of a fiber and a hole inside the paper M so that the direction of the internal diffuse reflection is considered to be isotropic. The optical intensity distribution of the internal diffuse reflection can be approximated to Lambert distribution.

To rotate a polarization direction by reflection by the paper M, the illumination has to be reflected by an inclined plane to a direction of the rotation relative to the optical axis. According to the present embodiment the center of the light source, that of illumination, and those of the light receivers are approximately on the same plane (detection plane) and a diffuse reflection whose polarization is rotated comes off from the detection plane so that they are not received at any light receiver. Thus, the polarizations of a specular reflection and a diffuse reflection and that of the illumination are in the same direction.

Meanwhile, the multiple diffuse reflections of light reflected by the paper M a number of times and internal diffuse reflection of light reflected inside the paper M a number of times may come off the detection plane by one reflection but be returned thereto by another reflection. Because of this, the multiple diffuse reflections and internal diffuse reflection traveling to the light receivers contain polarization components orthogonal to the polarization direction of the illumination.

Figure 6:
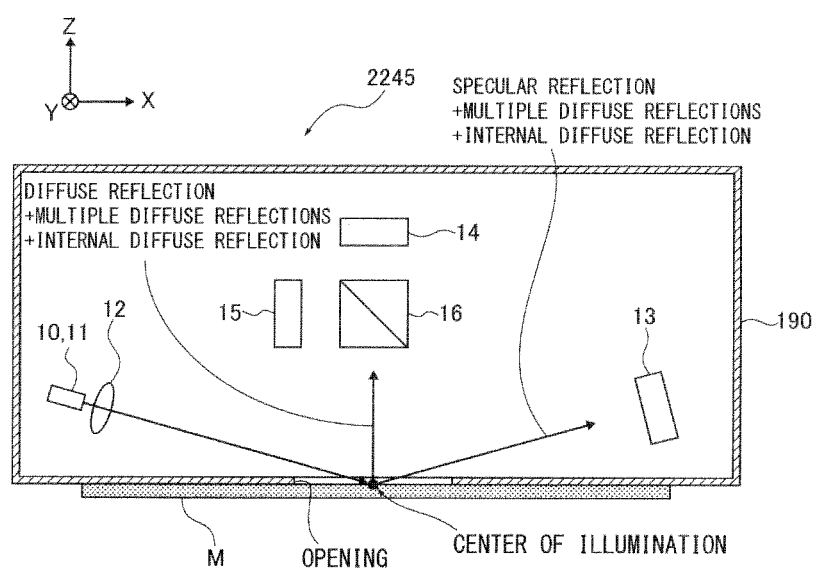
FIG. 6 shows a reflection of light to a polarization beam splitter and a reflection of light to a light receiver 13.

In FIG. 6 a diffuse reflection, multiple diffuse reflections and an internal diffuse reflection are incident on the polarization beam splitter 16.

Figure 7:
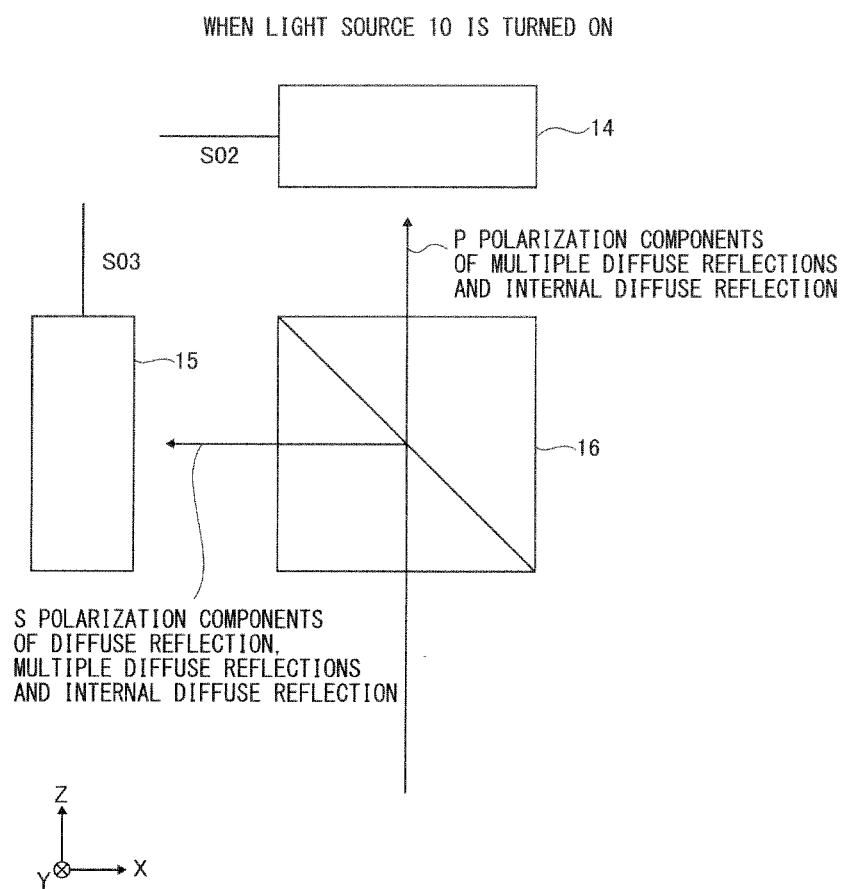

The diffuse reflection when the light source 10 turns on is a S polarization and reflected by the polarization beam splitter 16. The P polarization components of the multiple diffuse reflections and internal diffuse reflection transmit through the polarization beam splitter 16 while the S polarization components thereof are reflected by the polarization beam splitter 16. Thus, the light receiver 14 receives the P polarization components of the multiple diffuse reflections and internal diffuse reflection when the light source 10 turns on. The light receiver 15 receives the S polarization components of the diffuse reflection, multiple diffuse reflections and internal diffuse reflection, as shown in FIG. 7.

Figure 8:
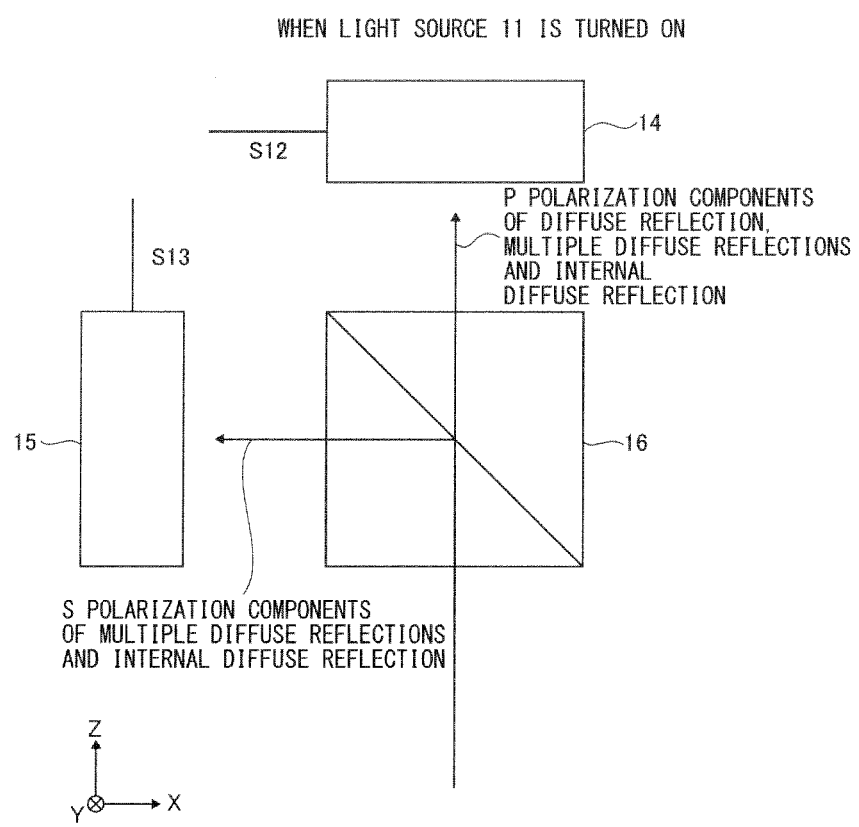

The diffuse reflection when the light source 11 turns on is a P polarization and transmits through the polarization beam splitter 16. The P polarization components of the multiple diffuse reflections and internal diffuse reflection transmit through the polarization beam splitter 16 while the S polarization components thereof are reflected by the polarization beam splitter 16. Thus, the light receiver 14 receives the P polarization components of the diffuse reflection, multiple diffuse reflections and internal diffuse reflection when the light source 11 turns on. The light receiver 15 receives the S polarization components of the multiple diffuse reflections and internal diffuse reflection, as shown in FIG. 8.

Figure 9A:
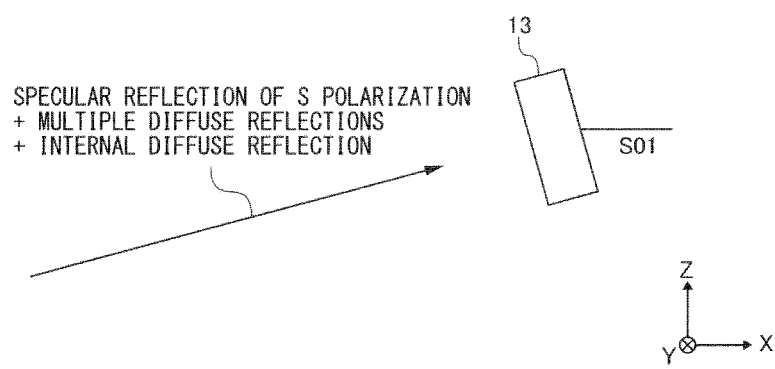
Figure 9B:
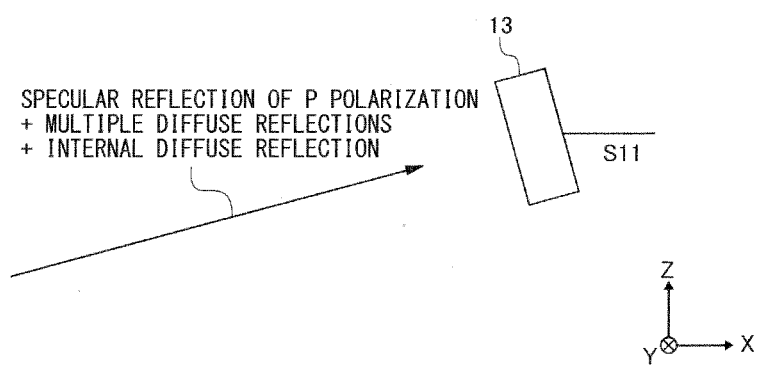

The light receiver 13 receives the specular reflection of a S polarization, multiple diffuse reflections, and internal diffuse reflection when the light source 10 turns on in FIG. 9A while it receives the specular reflection of a P polarization, multiple diffuse reflections, and internal diffuse reflection when the light source 11 turns on in FIG. 9B.

Each light receiver outputs an electric signal or photoelectric conversion signal corresponding to an amount of received light to the printer controller 2090.

In Reference 2 the type of a print object, presence or absence thereof, and its surface condition are electrically determined by separating a reflection of light from the printing object into S polarization components and P polarization components. Reference 2 utilizes the fact that the ratio of a reflection rate Rs of S polarization components and that Rp of P polarization components depends on the refractive index of a print object. The reflection rates Rs and Rp are expressed by the following formulas (1) and (2), respectively.

$$Rs = \left\{ \frac{\cos\theta - \sqrt{n^2 - \sin^2\theta}}{\cos\theta + \sqrt{n^2 - \sin^2\theta}} \times \exp\left(-\frac{4\pi\sigma\cos\theta}{\lambda}\right) \right\}^2 \qquad (1)$$

$$Rp = \left\{ \frac{n^2\cos\theta + \sqrt{n^2 - \sin^2\theta}}{n^2\cos\theta - \sqrt{n^2 - \sin^2\theta}} \times \exp\left(-\frac{4\pi\sigma\cos\theta}{\lambda}\right) \right\}^2 \qquad (2)$$

where n is a refractive index of an object, θ is an incidence angle, σ is a standard deviation of a surface roughness of the object, and λ is a wavelength of the illumination.

The reflection rate Rs can be found from the light amounts of the illumination of S polarization and a specular reflection of S polarization components. The reflection rate Rp can be found from the light amounts of the illumination of a P polarization and a specular reflection of a P polarization.

However, in Reference 2 since the detected reflection contains a reflection other than the specular reflection, a print object cannot be accurately determined.

In Reference 4 the surface inspection device is configured to inspect an object such as a semiconductor wafer having a much larger specular reflection rate than that of a paper so that it does not concern the multiple diffuse reflections and internal diffuse reflection at all.

According to the present embodiment the light amounts of specular reflections of a S polarization and a P polarization are more accurately found than related art.

Herein, levels of outputs signal of the light receivers 13, 14, 15 when the light source 10 turns on are set to S01, S02, and S03, respectively. Similarly, the levels of output signals of the light receivers 13, 14, 15 when the light source 11 turns on are set to S11, S12, and S13, respectively.

Further, with a mirror provided at the position of the paper M, levels of output signals of the light receiver 13 when the light sources 10, 11 turn on are set to S00 and S10, respectively.

S01 contains light amount information on a mixed reflection of a specular reflection of a S polarization, multiple diffuse reflections, and internal diffuse reflection. S02 contains light amount information on the P polarization components included in the multiple diffuse reflections and internal diffuse reflection. S03 contains light amount information on a mixed reflection of a diffuse reflection of a S polarization and the S polarization components included in the multiple diffuse reflections and internal diffuse reflection. S00 contains information on the light amount of the illumination of a S polarization.

S11 contains light amount information on a mixed reflection of a specular reflection of a P polarization, multiple diffuse reflections, and internal diffuse reflection. S12 contains light amount information on a mixed reflection of a diffused reflection of a P polarization, and the P polarization components of the multiple diffuse reflections and internal diffuse reflection. S13 contains light amount information on the S polarization components included in the multiple diffuse reflections and internal diffuse reflection. S10 contains information on the light amount of the illumination of a P polarization.

The multiple diffuse reflections and internal diffuse reflection are considered to include S polarization components and P polarization components at the same ratio.

The light amount of the multiple diffuse reflections and internal diffuse reflection by the paper M in +Z direction when the light source 10 turns on is 2×S02. Similarly, the light amount of the multiple diffuse reflections and internal diffuse reflection by the paper M in +Z direction when the light source 11 turns on is 2×S13.

Comparing the light amounts of the multiple diffuse reflections and the internal diffuse reflection by the paper M in +Z direction, the light amount of the multiple diffuse reflections is much smaller than that of the internal diffuse reflection. Also, the optical intensity distribution of the internal diffuse reflection can be approximated to Lambert distribution.

Accordingly, the light amount of the internal diffuse reflection by the paper M in specular direction when the light source 10 turns on is 2×S02×sin θ while the same when the light source 11 turns on is 2×S13×sin θ.

The light amount Ws1 of a specular reflection of a S polarization is calculated by the following formula (3):

$$Ws1 = S01 - 2 \times S02 \times \sin\theta \div A$$

where A is a correction coefficient for correcting a difference between the amplification rates of the light receivers 13 and 14 to convert a received light amount into an electric signal.

The light amount Wp1 of the specular reflection of a P polarization is calculated by the following formula (4):

$$Wp1 = S11 - 2 \times S13 \times \sin\theta \div B$$

where B a correction coefficient for correcting a difference between the amplification rates of the light receivers 13 and 15 to convert a received light amount into an electric signal. Here, A=B=200.

Then, the reflection rate Rs1 of the S polarization is calculated by the following formula (5):

$$Rs1 = Ws1 \div S00$$

The reflection rate Rp1 of the P polarization is calculated by the following formula (6):

$$Rp1 = Wp1 \div S10.$$

According to the present embodiment it is able to more accurately calculate the light amounts of the specular reflections of the S polarization and P polarization as well as the reflection rates of the S polarization and P polarization than related art. As seen from the formulas (1) and (2), the reflection rates depend on the refractive index and surface roughness of the paper M so that the paper M can be more accurately specified from the reflection rates Rs1. Rp1 than related art.

The ROM of the printer controller 2090 stores a paper determining table containing measured values of the reflection rates Rs1 and Rp1 for each brand of papers usable in the color printer 2000. The measured values are obtained in advance in a pre-shipping process such as adjustment process, for example.

Figure 10:
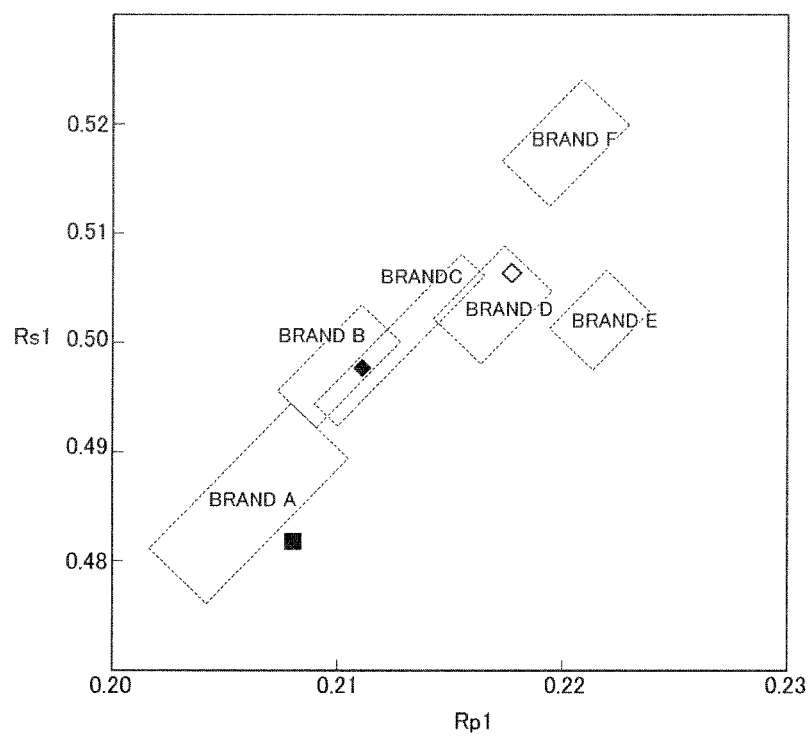
FIG. 10 is a graph showing a relation between Rs1 and Rp1 and paper brands.

FIG. 10 shows the measured values of Rs1 and Rp1 for several brands of papers available in Japan. In the drawing frames surrounded by broken lines indicate the area of a variation in each brand. For example, a brand D is specified from a measured value "◌" of Rs1 and Rp1. A brand A is specified from a measured value "■" since it is closest to the value. Either brand B or C is specified from a measured value "◌".

To choose one of the brands B and C, differences between average values and measured values of the brands B and C are calculated to determine a smaller difference as the right brand, for example. Alternatively, assumed that the brands B and C are specified, the variations B, C including the measured value in question can be re-calculated, to select one with a smaller variation.

The ROM of the printer controller 2090 stores a develop and transfer table containing optimal developing and transfer conditions for each station and for each brand of papers usable in the color printer 2000. The optimal conditions are determined in a pre-shipping process such as adjustment process.

Upon turning-on of the color printer 2000 or supply of sheets of paper into the paper tray 2060, for example, the printer controller 2090 determines a kind of the paper in the following manner.

1. Turn on the light source 10 of the optical sensor 2245.
2. Obtain an output signal of each light receiver.
3. Turn off the light source 10 of the optical sensor 2245.
4. Turn on the light source 11 of the optical sensor 2245.
5. Obtain an output signal of each light receiver.
6. Turn off the light source 11 of the optical sensor 2245.
7. Calculate Rs1 on the basis of an output signal of each light receiver when the light source 10 is turned on.
8. Calculate Rp1 on the basis of an output signal of each light receiver when the light source 11 is turned on.
9. Specify a brand of a paper from the values of Rs1 and Rp1, referring to the paper determining table.
10. Store the specified brand in the RAM and completes the paper determining process.

Upon receipt of a printing request from a user, the printer controller 2090 reads the brand of the paper from the RAM and acquires the optimal developing and transfer conditions for the brand from the develop and transfer table.

Then, it controls the developing unit and transfer unit of each station in accordance with the optimal developing and transfer conditions, for example, it controls transfer voltage and toner amount. Thereby, a high-quality image is formed on a paper.

Figure 11A:
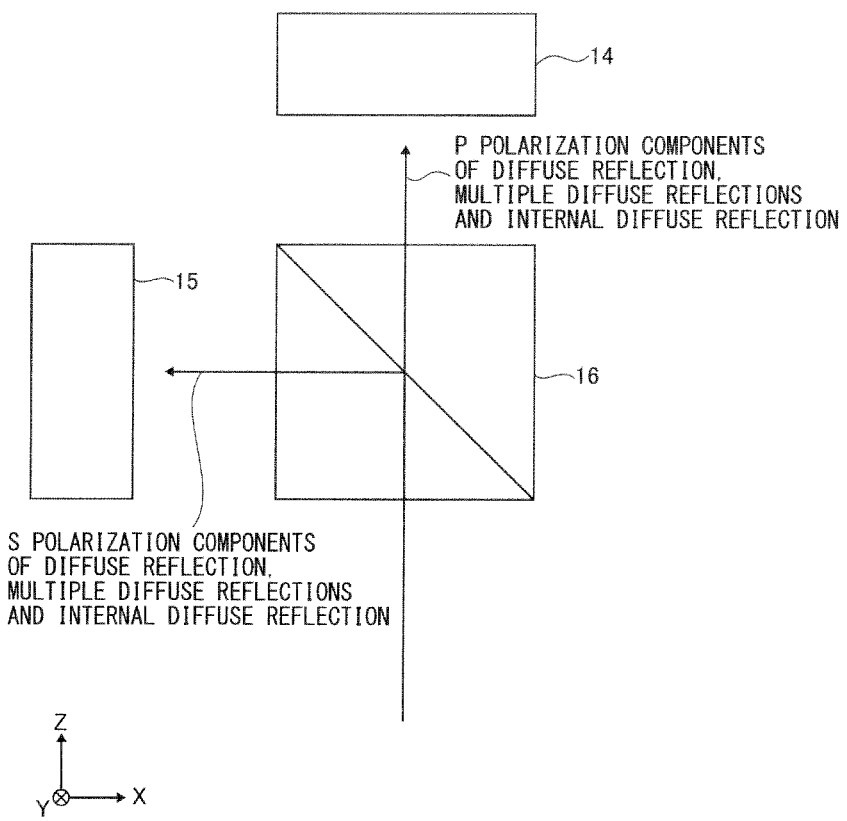

If the light sources 10 and 11 are concurrently turned on, the light receiver 14 receives the P polarization components included in the diffuse reflection, multiple diffuse reflections, and internal diffuse reflection. The light receiver 15 receives the S polarization components included in the diffuse reflection, multiple diffuse reflections, and internal diffuse reflection, as shown in FIG. 11A.

Figure 11B:
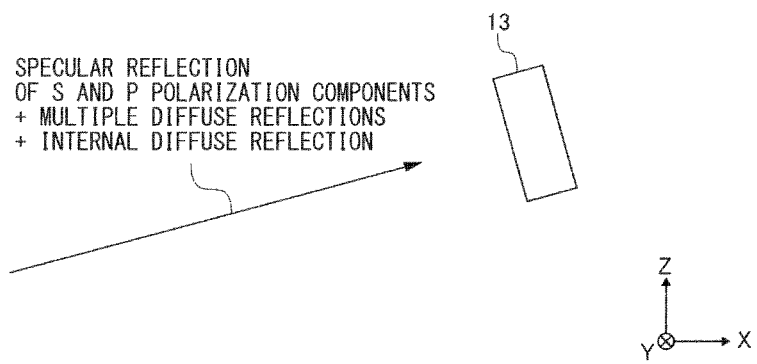

The light receiver 13 receives a specular reflection of S and P polarization components, and the multiple diffuse reflections and internal diffuse reflection, as shown in FIG. 11B.

In this case the light amounts of the specular reflections of the S and P polarizations components cannot be accurately found.

As described above, the optical sensor 2245 according to the present embodiment comprises the light sources 10, 11, collimate lens 12, light receivers 13-15, polarization beam splitter 16 and dark box 190.

The light source 10 illuminates a linear polarization of a S polarization and the light source 11 illuminates a linear polarization of a P polarization to the paper M. The polarization beam splitter 16 transmits the P polarization therethrough and reflects the S polarization. When the light source 10 is turned on, the light receiver 14 receives the P polarization components of the multiple diffuse reflections and internal diffuse reflection and the light receiver 15 receives the diffuse reflection of a S polarization and the S polarization components of the multiple diffuse reflections and internal diffuse reflection. When the light source 11 is turned on, the light receiver 14 receives a diffuse reflection of a P polarization and the P polarization components of the multiple diffuse reflections and internal diffuse reflection and the light receiver 15 receives the S polarization components of the multiple diffuse reflections and internal diffuse reflection. The light receiver 13 receives a mixed reflection of a specular reflection and the multiple diffuse reflections and internal diffuse reflection when any of the light sources 10, 11 is turned on.

Thus, the light amount of the specular reflection of the S polarization can be accurately calculated by the formula (3). Likewise, the light amount of the specular reflection of the P polarization can be accurately calculated by the formula (4). The reflection rate of the S polarization can be accurately calculated by the formula (5) and the reflection rate of the P polarization can be accurately calculated by the formula (6).

The color printer 2000 can thus improve the accuracy at which a brand of a paper is identified without an increase in the size and costs thereof.

The color printer 2000 incorporating the optical sensor 2245 can generate high-quality images without an increase in the size and costs thereof. Further, it can eliminate the necessity for troublesome manual settings and resolve printing failures caused by setting errors.

According to the present embodiment, in place of the polarization beam splitter 16, a polarization beam splitter 16' to transmit the S polarization components and reflect the P polarization can be provided.

Figure 12:
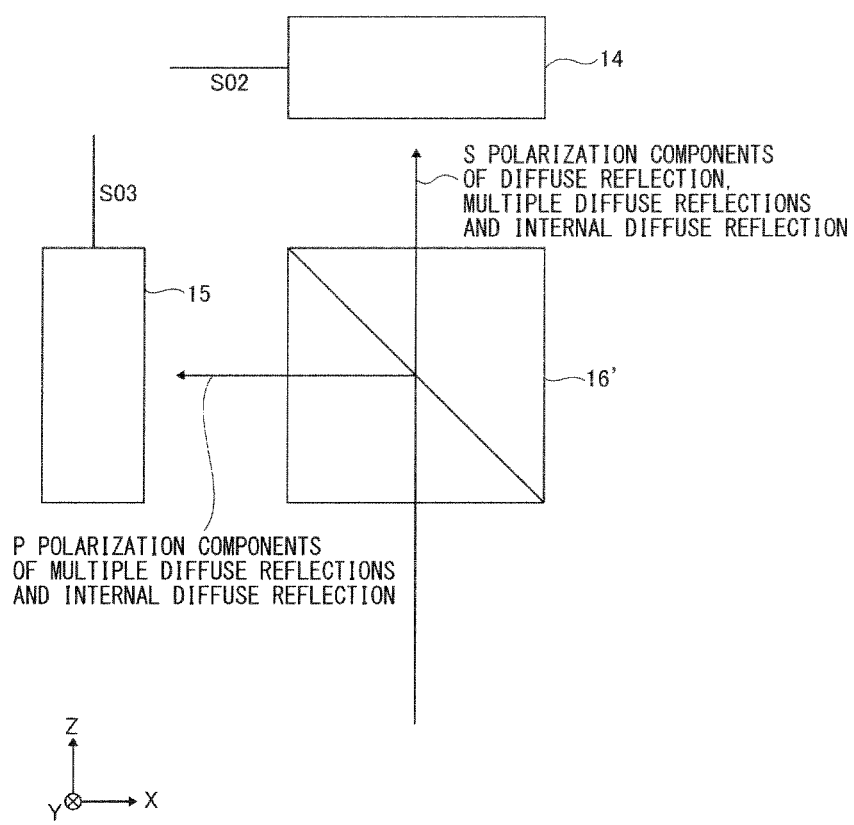

In this case, when the light source 10 is turned on, the light receiver 14 receives the S polarization components of the diffuse reflection, multiple diffuse reflections and internal diffuse reflection and the light receiver 15 receives the P polarization components of the multiple diffuse reflections and internal diffuse reflection, as shown in FIG. 12.

Figure 13:
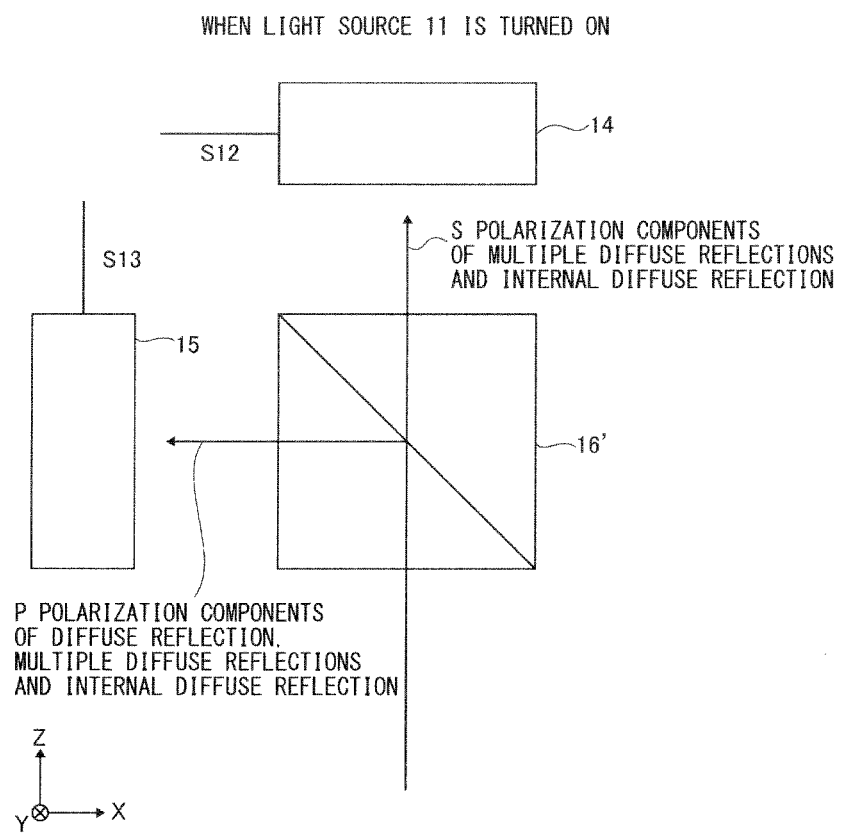

When the light source 11 is turned on, the light receiver 14 receives the S polarization components of the multiple diffuse reflections and internal diffuse reflection and the light receiver 15 receives the P polarization components of the diffuse reflection, multiple diffuse reflections and internal diffuse reflection, as shown in FIG. 13.

In place of the formulas (3) and (4), the following formulas (7), (8) are used.

$$Ws1 = S01 - 2 \times S03 \times \sin\theta \div B \tag{7}$$

$$Wp1 = S11 - 2 \times S12 \times \sin\theta \div A \tag{8}$$

Figure 14:
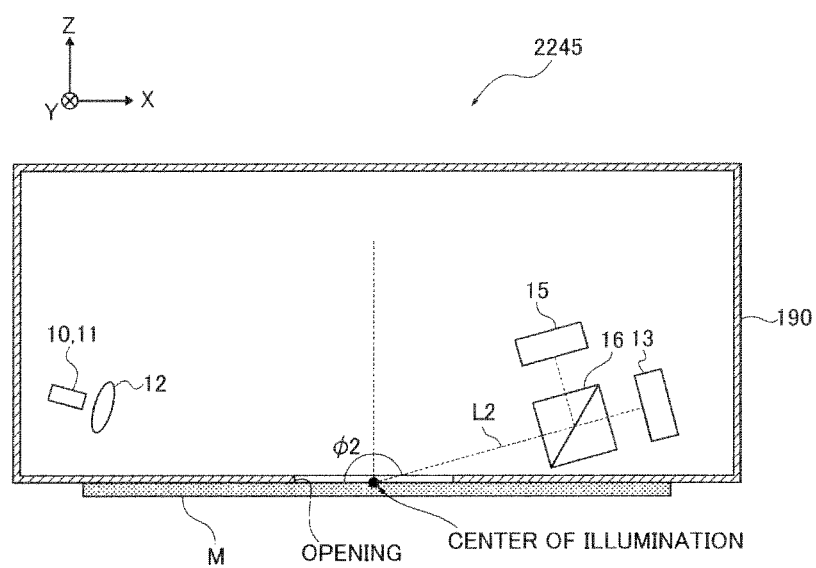
FIG. 14 shows another example of an optical sensor.

Further, according to the present embodiment, the polarization beam splitter 16 can be disposed on an optical path between the center of illumination and the light receiver 13 and the light receiver 15 can be disposed on an optical path of a reflection by the polarization beam splitter 16, as shown in FIG. 14. The light receiver 14 is unneeded.

Figure 15:
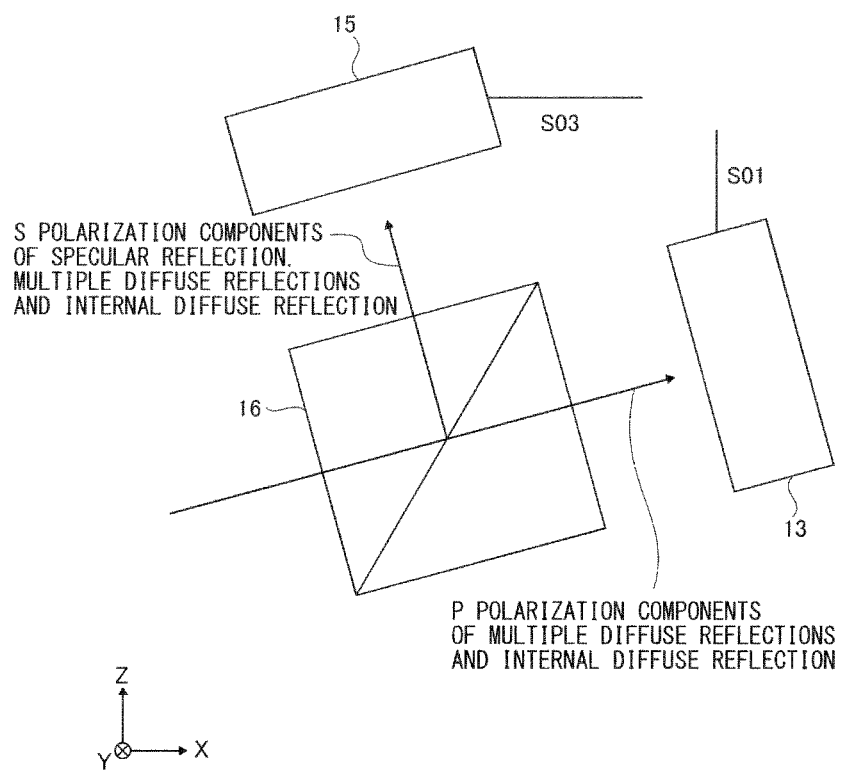

In this case, when the light source 10 is turned on, the light receiver 13 receives the P polarization components of the multiple diffuse reflections and internal diffuse reflection and the light receiver 15 receives the S polarization components of the specular reflection, multiple diffuse reflections and internal diffuse reflection, as shown in FIG. 15.

Figure 16:
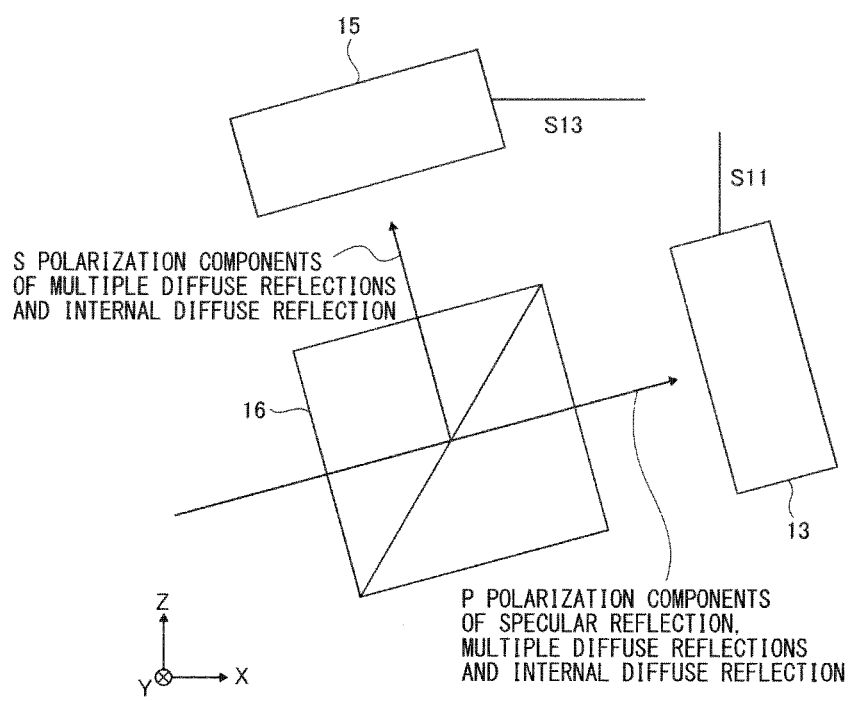

When light source 11 is turned on, the light receiver 13 receives the P polarization components of the specular reflection, multiple diffuse reflections and internal diffuse reflection and the light receiver 15 receives the S polarization components of the multiple diffuse reflections and internal diffuse reflection, as shown in FIG. 16.

The light amount Ws1 of the specular reflection of the S polarization is calculated by the formula (9). $Ws1 = S03 \div B - S01$ while that Wp1 of the specular reflection of the P polarization is calculated by the formula (10), $Wp1 = S11 - S13 \div B$.

Further, with a mirror provided at the position of the paper M, the light receiver 15 receives a specular reflection of the light beam from the light source 10, and a level of an output signal of the light receiver 15 is set to S30. The reflection rate Rs1 of the S polarization is calculated by the formula (11), Rs1=Ws1÷(S30÷B) and that Rp1 of the P polarization is calculated by the formula (6).

With a mirror provided at the position of the paper M, the light receiver 13 receives a specular reflection of the light beam from the light source 11, and a level of an output signal of the light receiver 13 is the same as S10 so that the reflection rate Rp1 of the P polarization is calculated by the formula (6).

According to the present embodiment, the incidence angle θ can be set to an arbitrary value other than 80 degrees. However, a small incidence angle such as 80 degrees is preferable. This is because at a small incidence angle the reflection rates of the S and P polarizations are increased in compliance with the Fresnel coefficient so that the S/N ratio of an output signal of each light receiver can be enlarged. Further, at a small incidence angle a difference in the refractive index and surface roughness greatly affects a difference in the reflection rate, thereby improving a resolution of the paper determination.

Further, in the present embodiment a condensing lens can be provided ahead of each light receiver to be able to reduce a variation in measured signal levels. Measuring reproducibility matters for the optical sensor which determines a paper on the basis of the light amount of reflection. The optical sensor is positioned on the assumption that the plane to be measured and the surface of the paper are on the same plane. However, the paper may be inclined or deflected relative to the measuring plane due to a warpage or oscillation. This causes a variation in the optical intensity distribution of reflected light and a change in a received light amount, making it hard to stably determine details of the paper. In view of this, condensing lenses are provided ahead of the light receivers to stabilize the received light amount irrespective of a change in the optical intensity distribution of the reflected light.

Moreover, for the purpose of resolving the problem that the measuring plane and the paper surface are not on the same plane, photo diodes (PD) having a large light-receiving area can be used for the light receivers or the beam diameter of the illumination can be narrowed.

Alternatively, PD arrays can be used for the light receivers. Thereby, a sufficiently large light receiving area as a whole relative to a shift amount in the intensity distribution of a reflection of light can be provided. The output level of each light receiver can be stabilized by using a maximal signal among signals detected by each PD even with a shift in the reflected light intensity distribution. Furthermore, reducing the light receiving area of each PD of the PD array can reduce a variation in the output caused by a difference between the incident light and the center of each light receiving area. Thereby, more accurate detection of the output level can be realized.

Figure 17:
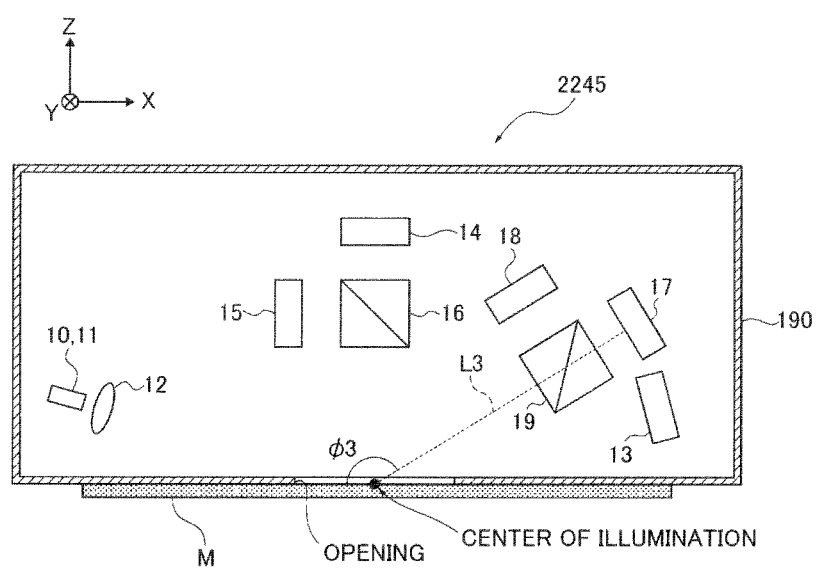
FIG. 17 shows another example of an optical sensor.

Further, two light receivers 17, 18 and a polarization beam splitter 19 can be additionally provided as shown in FIG. 17. The polarization beam splitter 19 transmits the P polarization and reflects the S polarization as the polarization beam splitter 16. The centers of the light receivers 17, 18 and the center of the polarization beam splitter 19 are on the detection plane. A line L3 connecting the center of illumination and the light receiver 17 and the surface of the paper M make an angle ψ3 of 150 degrees by way of example.

A diffuse reflection of the light beam from the light source 10 is a S polarization and reflected by the polarization beam splitter 19. The P polarization components of multiple diffuse reflections and internal diffuse reflection transmit through the polarization beam splitter 19 and the S polarization components thereof are reflected by the polarization beam splitter 19. Thus, the light receiver 17 receives the P polarization components of the multiple diffuse reflections and internal diffuse reflection and the light receiver 18 receives the S polarization components thereof, when the light source 10 is turned on.

A diffuse reflection of the light beam from the light source 11 is a P polarization and transmits through the polarization beam splitter 19. The P polarization components of multiple diffuse reflections and internal diffuse reflection transmit through the polarization beam splitter 19 and the S polarization components thereof are reflected by the polarization beam splitter 19. Thus, the light receiver 17 receives the P polarization components of the diffuse reflection, multiple diffuse reflections and internal diffuse reflection and the light receiver 18 receives the S polarization components of multiple diffuse reflections and internal diffuse reflection, when the light source 11 is turned on.

Herein, a level of an output signal of the light receiver 17 when the light source 10 is turned on is set to S04, and that of the light receiver 18 is S05. Similarly, a level of an output signal of the light receiver 17 when the light source 11 is turned on is set to S14, and that of the light receiver 18 is S15.

The light amount Ws2 of a specular reflection of the S polarization is calculated by the following formula (12):

$$Ws2 = S01 - 2 \times S02 \times \sin\theta \div A - 2 \times S04 \times \alpha \div C$$

where C is a correction coefficient for correcting a difference between the amplification rates of the light receivers 13 and 17 to convert a received light amount into an electric signal.

The light amount Wp2 of a specular reflection of the P polarization is calculated by the following formula (13):

$$Ws2 = S11 - 2 \times S13 \times \sin\theta \div B - 2 \times S15 \times \alpha \div D$$

where D is a correction coefficient for correcting a difference between the amplification rates of the light receivers 13 and 18 to convert a received light amount into an electric signal.

In the formulas (12) and (13) α is a value reflecting a direction distribution of the multiple diffuse reflections and unique to a direction (at angle ψ3) of the detection by the light receivers 17, 18 and the paper M. The values of α is measured in advance for each brand of the paper and contained in the paper determining table.

In the angle ψ3 direction the light amount of the multiple diffuse reflections is greatly larger than that of the internal diffuse reflection. Because of this, the light amount Ws2 of the specular reflection of the S polarization is more accurate than that Ws1 and the light amount Wp2 of the specular reflection of the P polarization is more accurate than that Wp1.

Figure 18:
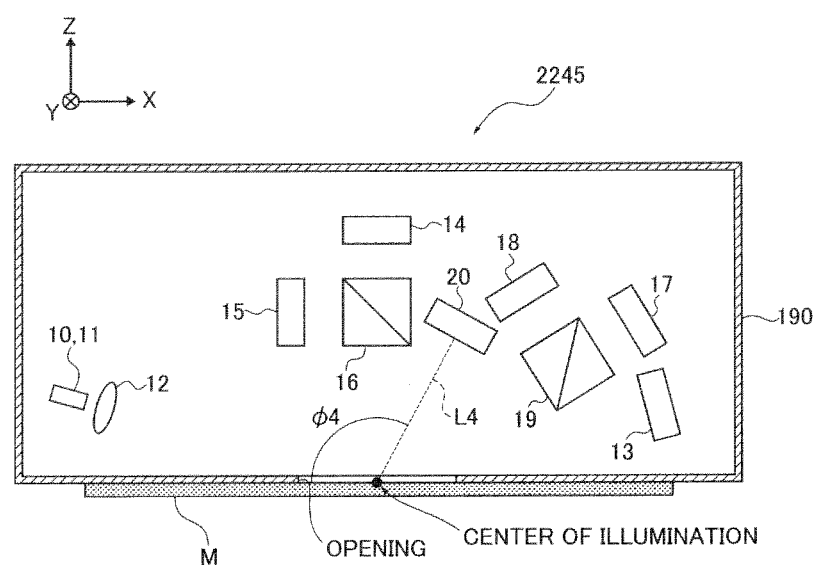
FIG. 18 shows still another example of an optical sensor.

The optical sensor 2245 can further comprise a light receiver 20 as shown in FIG. 18. The center of the light receiver 20 is on the detection plane and a line L4 connecting the center of the illumination and that of the light receiver 20 and the surface of the paper M make an angle of ψ4 of 120 degrees, for example.

By adding the outputs of the light receiver 20 in the paper determining table, the brand of the paper can be more accurately identified from the reflection rates of the S polarization and P polarization and the output of the light receiver 20.

Figure 19:
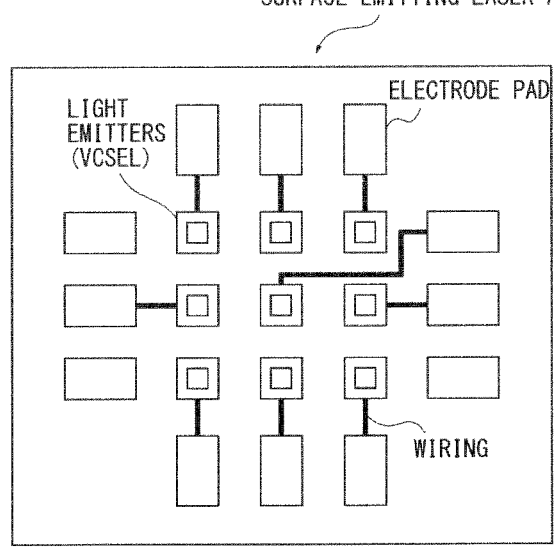
FIG. 19 shows the structure of a surface emitting laser array by way of example.

Further, the light sources 10, 11 can each include a plurality of light emitters. For example, it can include a vertical cavity surface emitting laser array (VCSEL array) in FIG. 19. This makes it easier to adjust the illumination to be a parallel light, resulting in decreasing the size and costs of the optical sensor.

However, there is a drawback that coherent lights from the light emitters are diffusely reflected by each point of the rough surface of the paper and interfere with each other to generate a speckle pattern.

Because the speckle pattern differs depending on a point on the illuminated surface, it causes a variation in the received light amounts of the light receivers and a decrease in the accuracy at which the light amounts are detected.

Figure 20:
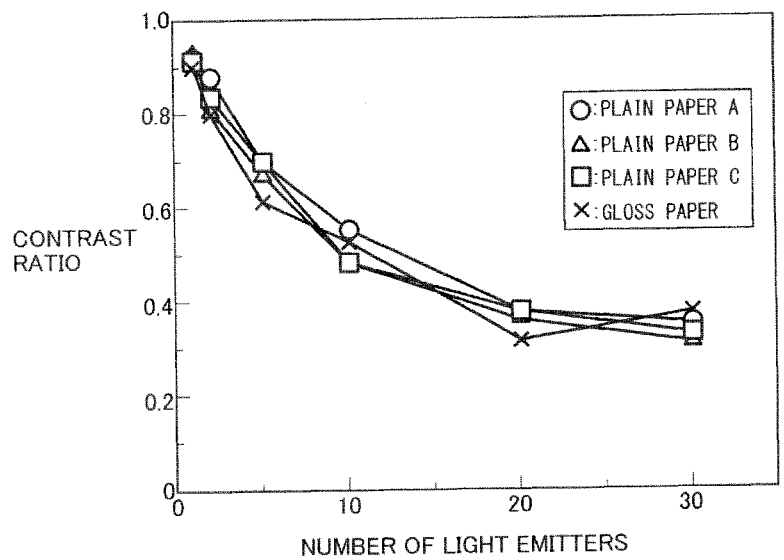
FIG. 20 is a graph showing a relation between the number of light emitters and the contrast ratio of a speckle pattern.

The inventors of the present invention found the relation between the number of light emitters and the contrast ratio of the speckle pattern by use of a surface emitting laser array in which light emitters are two-dimensionally arranged, as shown in FIG. 20. Here, the contrast ratio of the speckle pattern (hereinafter, simply contrast ratio) is defined to be a normalized value of a difference between the maximal and minimal values of measured intensities of the speckle pattern.

A beam profiler was placed in a diffuse direction to observe the speckle pattern and calculate the contrast ratio from the results of the observation. Three kinds of plain papers A to C with different smoothnesses and a gloss paper were used as specimen. The Ohken type smoothnesses of the papers A to C are 33, 50, and 100 seconds, respectively.

As seen from FIG. 20, the contract ratio decreases as the number of light emitters increases, and this does not depend on the type of a paper.

Further, the inventors conducted an experiment to confirm that the reduction in the contrast ratio occurred not by the increase in the total light amount but by the increase in the number of light emitters.

Figure 21:
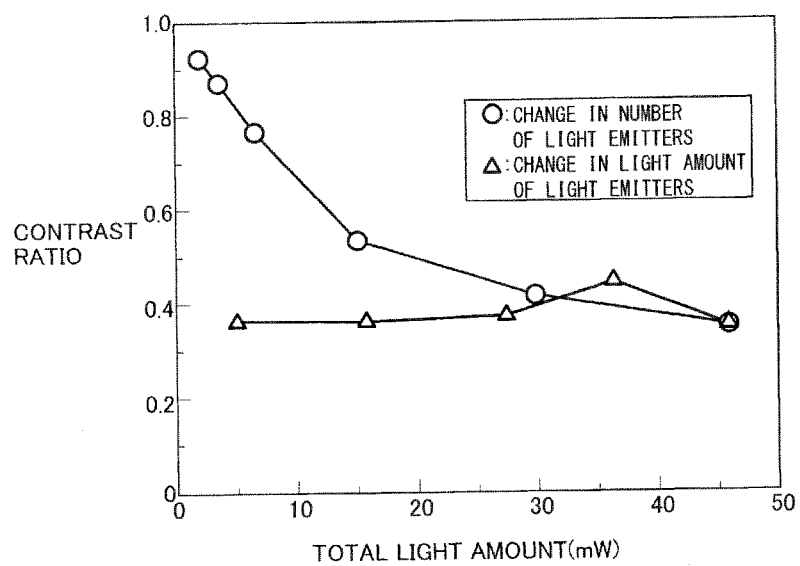
FIG. 21 is a graph showing a relation between the contrast ratio of a speckle pattern and a total light amount when the number of light emitters and the light amount of each of them are changed.

FIG. 21 is a graph showing the results of the experiment. It shows the relation between the total light amount and the contrast ratio when the number of emitters was changed with a light amount of each light emitter fixed to 1.66 mW and when the light amount of each light emitter was changed with the number thereof fixed to 30.

As seen from FIG. 21, when the number of light emitters was fixed and the light amount thereof was changed, the contrast ratio was constant irrespective of the light amount. Meanwhile, when the light amount was fixed and the number of light emitters was changed, the contrast ratio was large when the number of light emitters was small and the larger the number, the smaller the contrast ratio. Thus, it is confirmed that the reduction in the contrast ratio occurs not due to the increase in the light amount but due to the number of light emitters.

Further, the inventors studied the speckle pattern about if the speckle pattern could be reduced by temporally varying the wavelength of the light beam illuminated from the light source.

The wavelength of a light beam from a surface emitting laser can be controlled by a drive current. This is because with a change in the drive current, the temperature inside the surface emitting laser changes, changing a refractive index and an effective resonator length.

Figure 22:
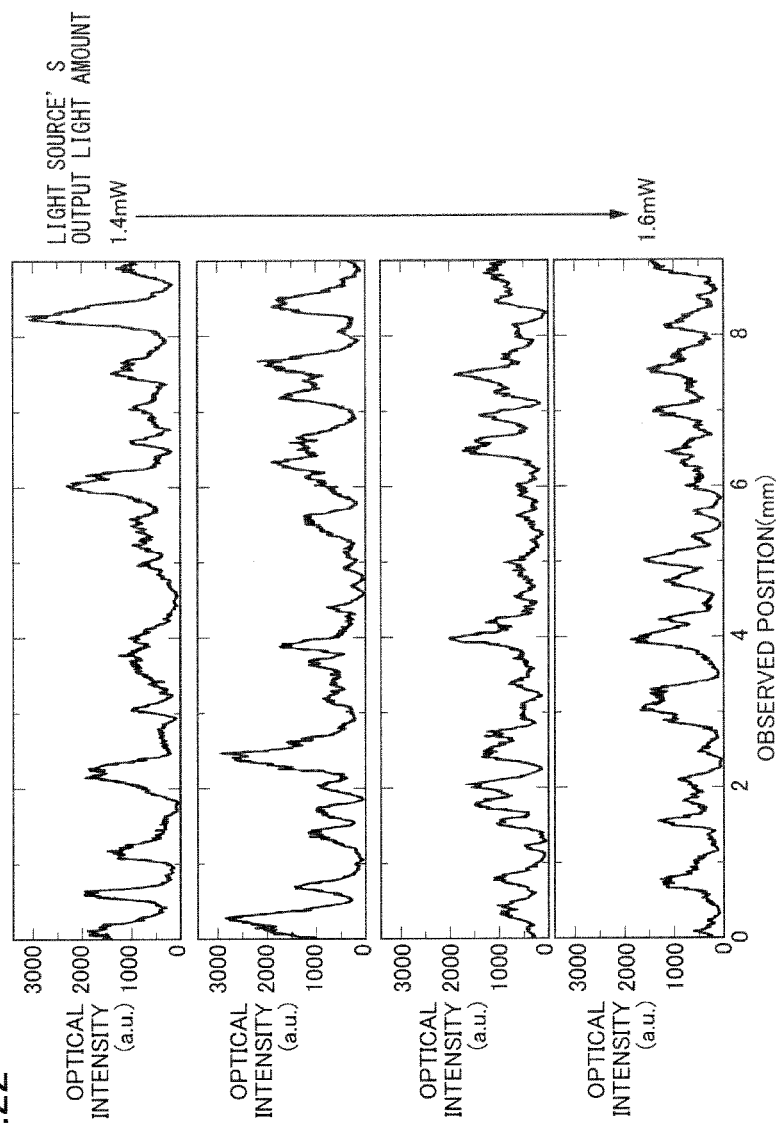
FIG. 22 shows the optical intensity distributions of a speckle pattern when the drive current of the surface emitting laser is changed.

FIG. 22 shows the optical intensity distribution of the speckle pattern observed with a beam profiler when the output light amount of the surface emitting laser was changed from 1.4 mW to 1.6 mW by changing the drive current. It can be confirmed from FIG. 22 that along with a change in the drive current or a change in the wavelength of the light beam from the surface emitting laser, the optical intensity distribution is changed.

Figure 23:
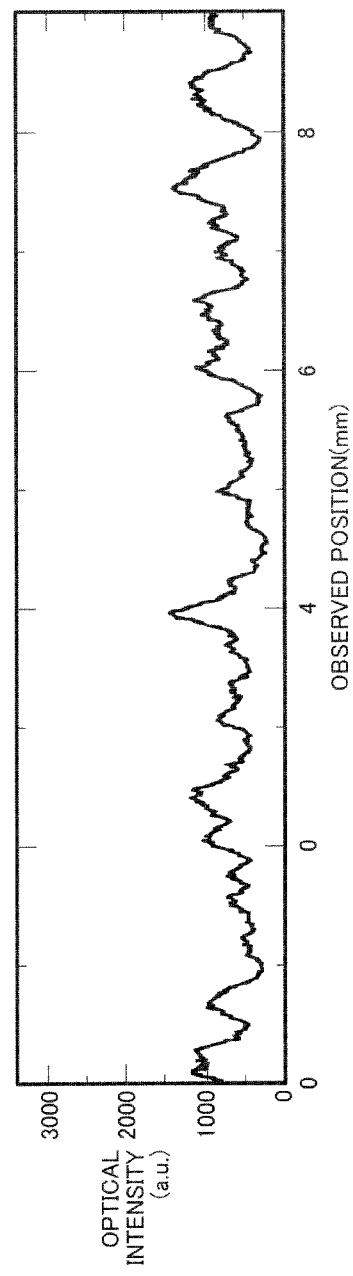
FIG. 23 shows an effective optical intensity distribution of a speckle pattern when the drive current of the surface emitting laser is changed at high speed.

FIG. 23 shows an effective optical intensity distribution when the drive current of the surface emitting laser was changed at high speed. This optical intensity distribution is equivalent to the average values of the optical intensity distribution by the change in the drive current in FIG. 22 and a variation in the optical intensity was reduced. The contrast ratio when the drive current was changed at high speed was 0.72 lower than that of 0.96 when the drive current was constant.

Thus, it was found that the speckle pattern was suppressed by temporally changing the wavelength of the illumination. Accordingly, the contrast ratio can be decreased by setting the drive current of the surface emitting laser to be in a triangular waveform whose current value temporally varies, for example.

Further, with the light sources 10, 11 including the surface emitting laser arrays, the CPU of the printer controller 2090 supplies the drive current with a triangular waveform to the surface emitting laser arrays. Thereby, it is able to suppress the speckle pattern, accurately detect the light amount of reflection and enhance the accuracy at which a paper is identified.

Figure 24:
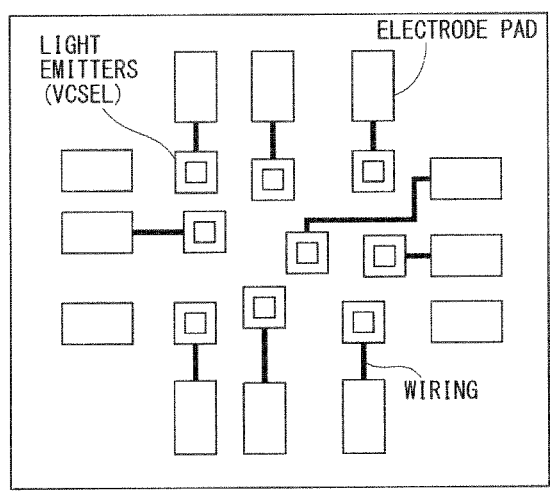
FIG. 24 shows another example of a surface emitting laser array.

Furthermore, the arrangement of the surface emitting laser array can be such that the interval among a part of the light emitters differs from the rest of them, as shown in FIG. 24. That is, the intervals between neighboring light emitters can be different from each other. This can disturb the regularity of the speckle pattern, further reducing the contrast ratio.

Alternatively, the surface emitting laser array can comprise light emitters to illuminate a P polarization of light and light emitters to illuminate a S polarization of light. Thereby, the light sources 10, 11 can be integrated.

Further, the inventors confirmed that the light amount of the internal diffuse reflection is correlated with the thickness and density of a paper. This is because the light amount of the internal diffuse reflection depends on a path length when passing through the paper. Thus, the brand of the paper can be specified from the reflection rate Rs1 of the S polarization and S02. In this case the light source 11 can be omitted. Similarly, it can be specified from the reflection rate Rp1 of the P polarization and S13 and the light source 10 can be omitted.

Further, the optical sensor 2245 can find the thickness and density of a target object including a sheet of paper on the basis of the light amount of a reflection including the internal diffuse reflection such as S02 and S13. Alternatively, it can adjust an image forming condition according to at least one of the thickness and density of the target object. However, it is necessary to prepare data indicating the relation between the light amount of the reflection including the internal diffuse reflection and the paper thickness and density and store it in the ROM of the printer controller 2090 as database. In related art a thickness sensor and a density sensor are of a transmissive type so that two optical systems need to be disposed on both sides of the target object, which requires a supporting member. Meanwhile, the optical sensor 2245 requires an optical system only on one side of the target object since it can detect the thickness and density from a reflection of light alone. Accordingly, it can be comprised of a less number of parts and elements, resulting in reducing the size and costs of the optical sensor.

Further, the refractive index and surface roughness of the target object can be found by assigning Rs1 to Rs of the formula (1) and Rp1 to Rp of the formula (2) and assigning specific values to the incidence angle θ and the wavelength λ of the illumination. The image forming condition can be adjusted in accordance with at least one of the refractive index and surface roughness.

Alternatively, the relation between the specular reflections of the S and P polarizations and the smoothness of the target object can be prepared and contained in the ROM of the printer controller 2090 as database. The image forming condition can be adjusted in accordance with the smoothness of the target object specified on the basis of the output of the optical sensor 2245, referring to the database.

Moreover, according to the present embodiment the optical sensor 2245 can include a processor configured to handle a part of the processing of the printer controller 2090.

In the present embodiment the number of the paper tray is 1 but it can be two or more and the optical sensor 2245 can be provided for each paper tray.

Further, the optical sensor 2245 can be placed near a carrier path, for example, between the feed roller 2054 and transfer roller 2042 in order to specify the brand of a paper during a paper feed.

Further, an object to be identified by the optical sensor 2245 is not limited to sheets of paper.

The above embodiment has described the color printer 2000 as one example of the image forming device. Alternatively, it can be a monochrome laser printer or an image forming device other than a printer such as a copier, a facsimile machine, or a multifunction peripheral including such machines.

The above embodiment has described the image forming device having four photoreceptor drums by way of example. Alternatively, it can be a printer having five photoreceptor drums.

Further, the above embodiment has described the image forming device which transfers a toner image from the photoreceptor drums to a paper via the transfer belt. Alternatively, it can be an image forming device which directly transfers a toner image from the photoreceptor drums to a paper.

Further, the optical sensor 2245 is applicable to an inkjet type image forming device.

Although the present invention has been described in terms of exemplary embodiments, it is not limited thereto. It should be appreciated that variations or modifications may be made in the embodiments described by persons skilled in the art without departing from the scope of the present invention as defined by the following claims.

What is claimed is:

1. An optical sensor comprising:
a light source to illuminate an object with light of a first linear polarization;
a first optical detector disposed on a path of the light illuminated from the light source and specularly reflected by the object, light detected by the first optical detector including reflection light from a surface of the object and reflection light from inside the object;
a first optical element to separate the light reflected by the object into the first linear polarization in a first direction and a second linear polarization in a second direction orthogonal to the first direction;
a second optical detector to receive the second linear polarization in the second direction separated by the first optical element;
a third optical detector to receive the first linear polarization in the first direction separated by the first optical element; and
a processor to (i) obtain an amount of specular reflection of the first linear polarization by the object on the basis of an output signal of the first optical detector and an output signal of the second optical detector, (ii) obtain an amount of specular reflection of the second linear polarization on the basis of the output signal of the first optical detector and an output signal of the third optical detector, (iii) calculate a reflection rate of the first linear polarization based on the obtained amount of specular reflection of the first linear polarization, (iv) calculate a reflection rate of the second linear polarization based on the obtained amount of specular reflection of the second linear polarization, and (v) determine a material type of the object based on the reflection rate of the first linear polarization and the reflection rate of the second linear polarization.

2. The optical sensor according to claim 1, wherein the first optical element is disposed on a path of a light diffused by the object in a normal direction relative to a surface of the object.

3. The optical sensor according to claim 2, wherein the processor calculates the amount of the light specularly reflected by the object, by the following formula:

$$S01-2\times S02\times \sin\theta \div A$$

where S01 is an output level of the first optical detector, S02 is an output level of the second optical detector, A is a correction coefficient for correcting a difference between amplification rates of the first and second optical detectors, and θ is an incidence angle of the light illuminated from the light source on the object.

4. The optical sensor according to claim 2, further comprising
another light source which illuminates another linear polarization in the second direction,
wherein when the object is illuminated with said another linear polarization in the second direction from said another light source, the processor obtains a light amount of the second linear polarization in the second direction specularly reflected by the object on the basis of output signals of the first and third optical detectors.

5. The optical sensor according to claim 4, wherein the processor calculates the light amount of the second linear polarization in the second direction specularly reflected by the object, by the following formula:

$$S11-2\times S13\times \sin\theta \div B$$

where S11 is an output level of the first optical detector and S13 is an output level of the third optical detector when the object is illuminated with said another linear polarization from said another light source in the second direction, B is a correction coefficient for correcting a difference between amplification rates of the first and third optical detectors, and θ is an incidence angle of the light illuminated from said another light source on the object.

6. The optical sensor according to claim 1, further comprising a collimate lens disposed on a path of the light illuminated from the light source.

7. The optical sensor according to claim 1, wherein the light source includes a surface emitting laser array having light emitters.

8. The optical sensor according to claim 7 wherein the light emitters are two-dimensionally arranged.

9. The optical sensor according to claim 7, wherein in one direction, an interval with which at least a part of the light emitters are arranged is different from an interval with which a rest of the light emitters are arranged.

10. The optical sensor according to claim 7, further comprising a system to temporally change a wavelength of the light illuminated from the light source.

11. The optical sensor according to claim 10, wherein the system is configured to temporally change the wavelength of the light illuminated from the light source by temporally changing a magnitude of a drive current supplied to the light source.

* * * * *